United States Patent
Benson et al.

(10) Patent No.: US 10,639,167 B2
(45) Date of Patent: May 5, 2020

(54) ELECTRICALLY STIMULATED BONE GRAFTING SPINAL IMPLANT SYSTEM AND METHOD

(71) Applicant: Warsaw Orthopedic, Inc., Warsaw, IN (US)

(72) Inventors: Nicholas M. Benson, Collierville, TN (US); Newton H. Metcalf, Memphis, TN (US); Steven D. Glassman, Louisville, KY (US); Shane Burch, San Anselmo, CA (US); Domagoj Coric, Charlotte, NC (US); Robert A Fields, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 23 days.

(21) Appl. No.: 16/039,632

(22) Filed: Jul. 19, 2018

(65) Prior Publication Data

US 2019/0321181 A1    Oct. 24, 2019

Related U.S. Application Data

(63) Continuation-in-part of application No. 14/792,256, filed on Jul. 6, 2015, now Pat. No. 10,123,882.

(51) Int. Cl.
*A61F 2/44* (2006.01)
(52) U.S. Cl.
CPC .................................. *A61F 2/447* (2013.01)
(58) Field of Classification Search
CPC ........ A61F 2/44; A61F 2/4425; A61F 2/4455; A61F 2/446; A61F 2/4465; A61F 2/447; A61F 2002/4435; A61F 2002/444; A61F 2002/4475; A61F 2002/448; A61F 2002/4485; A61F 2002/449; A61F 2002/4495

See application file for complete search history.

(56) References Cited

U.S. PATENT DOCUMENTS

| | | | |
|---|---|---|---|
| 4,781,591 A | 11/1988 | Allen | |
| 5,383,935 A * | 1/1995 | Shirkhanzadeh | ........ A61C 8/00 433/173 |
| 6,120,502 A * | 9/2000 | Michelson | ......... A61B 17/1671 606/247 |
| 6,292,699 B1 | 9/2001 | Simon et al. | |
| 7,455,672 B2 | 11/2008 | Michelson | |

(Continued)

FOREIGN PATENT DOCUMENTS

WO    84-01298 A1    4/1984

OTHER PUBLICATIONS

Patient Guide to Bone Growth Stimulation, <https://www.spineuniverse.com/resource-center/bone-growth-stimulation/patient-guide-bone-growth-stimulation>, Gerard J./Girasole, MD.

(Continued)

*Primary Examiner* — Eric S Gibson

(57) ABSTRACT

A spinal implant system includes bone growth promoting material, and an electrical bone growth stimulator. The electrical bone growth stimulator includes a mesh that surrounds at least a portion of the bone growth material, and the electrical bone growth stimulator is configured to conduct an electric current to stimulate tissue growth adjacent to the electrical bone growth stimulator.

20 Claims, 7 Drawing Sheets

(56) References Cited

U.S. PATENT DOCUMENTS

| | | | |
|---|---|---|---|
| 8,147,549 B2* | 4/2012 | Metcalf, Jr. | A61B 5/0031 |
| | | | 623/17.11 |
| 8,494,644 B2 | 7/2013 | Cowan et al. | |
| 8,838,249 B2 | 9/2014 | Nycz | |
| 8,945,226 B2* | 2/2015 | Johnston | A61F 2/447 |
| | | | 623/17.16 |
| 9,408,718 B2* | 8/2016 | Johnston | A61F 2/447 |
| 10,123,882 B2* | 11/2018 | Stevenson | A61F 2/447 |
| 2011/0118852 A1 | 5/2011 | Evans | |
| 2011/0160860 A1* | 6/2011 | Johnston | A61F 2/447 |
| | | | 623/17.16 |
| 2012/0316649 A1* | 12/2012 | Johnston | A61F 2/447 |
| | | | 623/17.16 |
| 2014/0114382 A1* | 4/2014 | Kim | A61L 27/047 |
| | | | 607/116 |
| 2014/0212471 A1 | 7/2014 | Drapeau et al. | |
| 2015/0190242 A1 | 7/2015 | Blain et al. | |
| 2016/0270927 A1* | 9/2016 | Zellmer | A61F 2/4455 |
| 2017/0007420 A1* | 1/2017 | Stevenson | A61F 2/447 |
| 2019/0009083 A1* | 1/2019 | Webster | A61N 1/326 |
| 2019/0133778 A1* | 5/2019 | Johnston | A61F 2/447 |

OTHER PUBLICATIONS

Mast MidLF Procedure, Midline Lumbar Fusion Surgical Technique Featuring the Gen 2.0 Retractor System, 2013, PMD 0009766-2.0 28676.

Bone Grafting Options—Categorization Guide, 2011, Medtronic Sofamor Danek, USA, Inc., PMD0012828-2.0 UC201203649IE.

\* cited by examiner

ELECTRICALLY STIMULATED BONE GRAFTING SPINAL IMPLANT SYSTEM AND METHOD

RELATED APPLICATIONS AND CLAIM OF PRIORITY

This patent document claims priority to, and is a continuation-in-part of, U.S. patent application Ser. No. 14/792,256, filed Jul. 6, 2015, the disclosure of which is fully incorporated in its entirety into this document by reference.

TECHNICAL FIELD

The present disclosure generally relates to medical devices for the treatment of musculoskeletal disorders, and more particularly to a surgical system and method for treating a spine.

BACKGROUND

Spinal pathologies and disorders such as degenerative disc disease, disc herniation, osteoporosis, spondylolisthesis, stenosis, tumor, scoliosis and other curvature abnormalities, kyphosis and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, partial or complete discectomy, corpectomy and laminectomy, and implantable prosthetics. As part of these surgical treatments, spinal constructs, such as, for example, bone fasteners, spinal rods and interbody devices can be used to provide stability to a treated region. For example, during surgical treatment, implants can be delivered to a surgical site for fixation with bone to immobilize a joint. Such implants can include bone growth promoting material, such as bone graft tissue, to enhance fixation of the implants with the bone. This disclosure describes an improvement over these technologies.

SUMMARY

The example embodiments of the surgical system and related methods of use disclosed are discussed in terms of medical devices for the treatment of musculoskeletal disorders and more particularly, in terms of a surgical system including a spinal implant and a method for treating a spine. In some embodiments, the surgical systems and methods of the present disclosure are employed with a spinal joint for purposes of obtaining or enhancing fusion, for example, with a cervical, thoracic, lumbar and/or sacral region of a spine.

In some embodiments, the surgical system includes an implant, such as, for example, an implant. In some embodiments, the implant includes an electrical bone growth stimulation interbody device.

In some embodiments, the surgical system includes an implant including electronic components that generate an electric current to stimulate bone growth. In some embodiments, the electronic components include diagnostics that provide diagnostic feedback and/or measure at least one diagnostic condition. In some embodiments, the diagnostics include, for example, embedded sensors for strain, stress and/or temperature. In some embodiments, the electronic components include remote power options using telemetry, such as, for example, near-field communication (NFC). In some embodiments, the electronic components include coils located outside a patient for powering the electronic components. In some embodiments, the electronic components include a NFC power harvesting integrated circuit. In some embodiments, the electronic components include an analog front end integrated circuit. In some embodiments, the electronic components include a microprocessor integrated circuit.

In some embodiments, the surgical system includes an implant including electronic components that generate an electric field adjacent to and encompass a selected region of spinal tissue to stimulate bone growth. In some embodiments, the electronic components include one or more electrodes disposed in a configuration to generate an electric field over a selected region of spinal tissue to stimulate bone growth. In some embodiments, the electronic components include two electrodes configured to generate an elliptical electric field over a selected region of spinal tissue to stimulate bone growth. In some embodiments, the electronic components include one or more external devices, such as, for example, a tablet, computer and/or healthcare database that remotely communicate, such as via short-range technology, wireless technology, Bluetooth technology, NFC technology and/or the transmission/reception of radio-frequency (RF) signals with the implant. In some embodiments, the electronic components include micro-electronic systems, which may include micro-electronic substrates, a leadless stimulator placed in the implant, and/or a hermetically sealed pressure sensor. In some embodiments, the electronic components include titanium cathode and anode windows placed in an implant for galvanic current and/or galvanic coupling across a graft space.

In some embodiments, the surgical system includes an implant including integration of electronic components into the implant to monitor patient's recovery and may include an accelerometer, temperature sensor, strain gauge and/or a magnetometer. In some embodiments, the implant includes electrical bone growth stimulation by implanting an implant with a small circuit and an electrode; the circuit being powered from an external device via telemetry (NFC, for example). In some embodiments, the implant comprises a bio-absorbable or partially bio-absorbable bone growth stimulator. In some embodiments, the implant stimulates bone growth and comprises multiple porous cathodes.

In some embodiments, the surgical system includes an implant with electronic components having variable power settings. In some embodiments, the surgical system includes an implant with electronic components that sense or detect impedance and/or collect impedance measurements as a proxy/indicator of fusion and may reduce the need or exposure to harmful radiation such as, for example x-ray or fluoroscopy. In some embodiments, the surgical system includes an implant with electronic components that take diagnostic measurements from onboard sensors of an interbody cage. In some embodiments, the electronic components monitor diagnostic measurements of impedance or interpreting such impedance measurements as an indication of bone density and/or bone growth/fusion through/onto/around the implant. In certain embodiments temperature may be sensed or measured to assess potential stress, inflammation, or infection.

In an embodiment, a spinal implant system includes bone growth promoting material, and an electrical bone growth stimulator. The electrical bone growth stimulator includes a first end, a second end and a body portion disposed between the first end and the second end. The electrical bone growth stimulator is positioned across a portion of the bone growth material, and the electrical bone growth stimulator is configured to conduct an electric current to stimulate tissue growth adjacent to the electrical bone growth stimulator.

In an embodiment, the bone growth promoting material comprises one or more of the following: synthetic bone grafting material, allograft bone grafting material, or bone morphogenetic protein material. The electrical bone growth stimulator may include a cathode rod.

In an embodiment, the spinal implant system may include a control unit and an anode. The control unit may be configured to communicate with a remote controller. The electrical bone growth stimulator may be configured to be powered by a remote control unit.

In various embodiments, the control unit may include one or more diagnostic sensors that are configured to detect impedance between the electrical bone growth stimulator and a remote anode.

In an embodiment, a spinal implant system includes bone growth promoting material, and an electrical bone growth stimulator. The electrical bone growth stimulator includes a mesh that surrounds at least a portion of the bone growth material, and the electrical bone growth stimulator is configured to conduct an electric current to stimulate tissue growth adjacent to the electrical bone growth stimulator.

In some embodiments, the bone growth promoting material may include one or more of the following: synthetic bone grafting material; allograft bone grafting material; or bone morphogenetic protein material.

The spinal implant system may include a control unit and an anode. The control unit may be configured to communicate with a remote controller. In certain embodiments, the electrical bone growth stimulator may be configured to be powered by a remote control unit.

In some embodiments, the control unit may include one or more diagnostic sensors that are configured to detect impedance between the electrical bone growth stimulator and a remote anode.

In an embodiment, a bone graft includes bone growth promoting material, and an electrical bone growth stimulator that includes cathode material. The electrical bone growth stimulator is positioned across at least a portion of the bone growth material, and the electrical bone growth stimulator is configured to conduct an electric current to stimulate tissue growth adjacent to the electrical bone growth stimulator.

The bone growth promoting material includes one or more of the following: synthetic bone grafting material, allograft bone grafting material, or bone morphogenetic protein material.

In certain embodiments, the electrical bone growth stimulator comprises a cathode rod. In other embodiments, the electrical bone growth stimulator comprises a cathode mesh.

The bone graft may include a control unit and an anode. The control unit may be configured to communicate with a remote controller. The control unit may include one or more diagnostic sensors that are configured to detect impedance between the electrical bone growth stimulator and a remote anode.

BRIEF DESCRIPTION OF THE DRAWINGS

The present disclosure will become more readily apparent from the specific description accompanied by the following drawings, in which.

DETAILED DESCRIPTION

Figure 1:
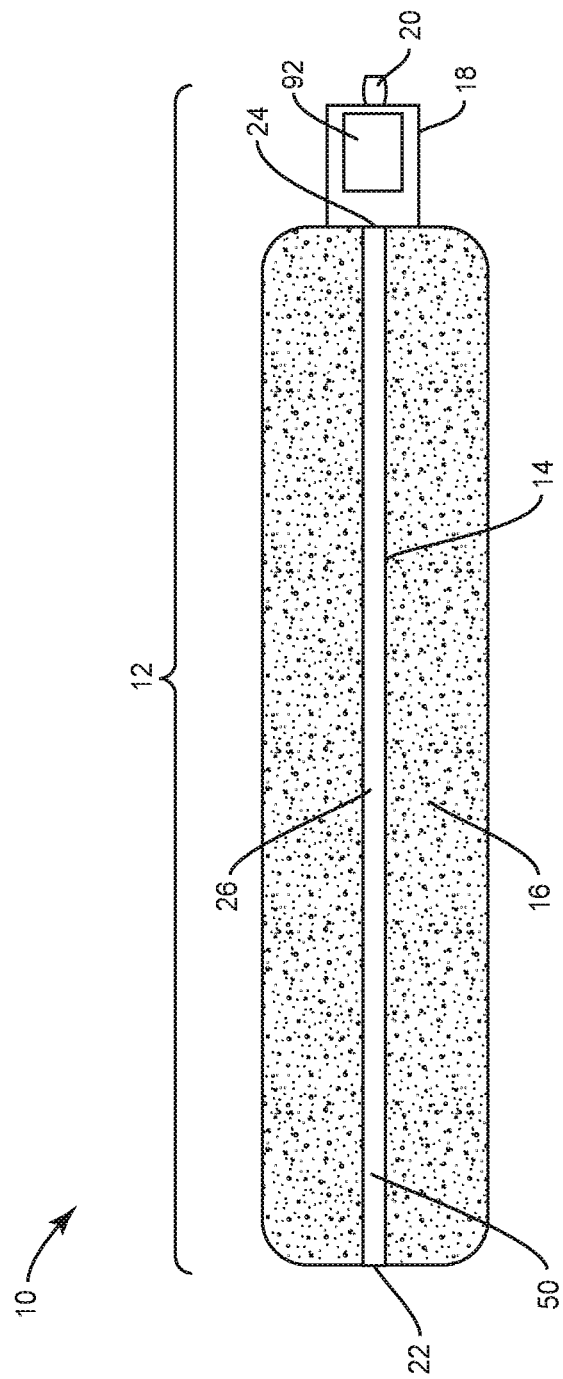
FIG. 1 illustrates an example spinal implant system according to an embodiment.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, muscle, ligaments, tendons, cartilage and/or bone unless specifically referred to otherwise.

Figure 2:
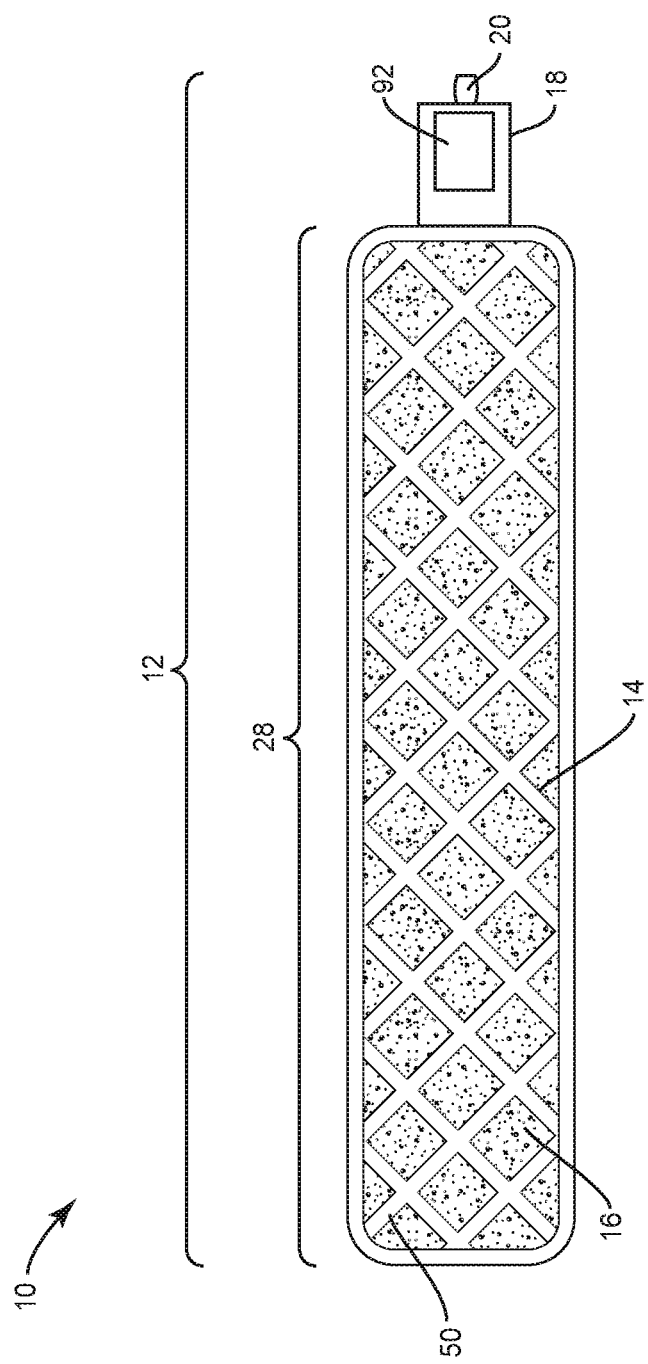
FIG. 2 illustrates an example spinal implant system according to an embodiment.

The following discussion includes a description of a surgical system and related methods of employing the surgical system in accordance with the principles of the present disclosure. Alternate embodiments are also disclosed. Reference is made in detail to the example embodiments of the present disclosure, which are illustrated in the accompanying figures. Turning to FIGS. 1 and 2, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites, unless specifically referred to otherwise. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, silver alloys, copper alloys, gold alloys, super-elastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including PEEK, polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-.beta.), osteoblast cells, growth and differentiation factor (GDF), insulin-like growth factor 1, platelet-derived growth factor, fibroblast growth factor, or any combination thereof.

Various components of spinal implant system 10 may have material composites, including the above materials, to achieve various desired characteristics such as conductivity, insulation and/or electrical isolation, strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein, in one embodiment, a spinal implant, as described herein, may be formed substantially of a biocompatible metal, such as titanium and selectively coated with a bone-growth promoting material, such as HA. In one embodiment, a spinal implant, as described herein, may be formed substantially of a biocompatible polymer, such as PEEK, and selectively coated with a biocompatible metal, such as titanium, or a bone-growth promoting material, such as HA. In some embodiments, titanium may be plasma sprayed onto surfaces of the spinal implant to modify a radiographic signature of the spinal implant and/or improve bony ongrowth to the spinal implant by application of a porous or semi-porous coating of titanium.

Spinal implant system 10 may be employed, for example, with minimally invasive procedures, including percutaneous techniques, mini-open surgical techniques and/or open surgical techniques to deliver and introduce implants, such as, for example, an implant, at a surgical site within a subject body of a patient, which includes, for example, a spine. In some embodiments, the implant can include spinal constructs including one or more bone fasteners, spinal rods, connectors and/or plates. In some embodiments, spinal implant system 10 includes one or a plurality of selected implants for a particular surgical procedure. In some embodiments, spinal implant system 10 includes one or a plurality of implants selectively personalized to a patient. The implant 12 may be configured to be placed posterolaterally, anteriorly, posteriorly, laterally, and/or obliquely into the spine.

Spinal implant system 10 comprises a spinal implant 12, such as, for example, an implant or other type of implant. Implant 12 includes an electrical bone growth stimulator 14, and a bone growth promoting material 16. The implant 12 may be implemented as a prefabricated grafting solution that includes an electrical bone growth stimulator as described in this disclosure. In various embodiments, the spinal implant system 10 includes a control unit 18 and an anode 20.

FIG. 1 illustrates an embodiment where an electrical bone growth stimulator 14 is implemented as a cathode rod. In this implementation, an electrical bone growth stimulator 14 may have a first end 22 and a second end 24 and a body portion 26 disposed between. In some embodiments, the electrical bone growth stimulator 14 may have a length of approximately 4-30 cm.

As illustrated by FIG. 1, the electrical bone growth stimulator 14 is positioned in bone growth promoting material 16 geometry. For instance, an electrical bone growth stimulator 14 may extend across a length of bone growth promoting material. In various embodiments, bone growth promoting material 16 may include bone graft to enhance fixation of the components and/or surfaces of spinal implant system 10 with vertebrae. Examples of bone growth promoting material 16 includes, without limitation, synthetic bone grafting technology, allograft bone grafting technology, bone morphogenetic protein technology, MagniFuse® bone grafting products, and/or the like. In various embodiments, bone growth promoting material may have an approximate length of up to 30 mm, which may be in approximately 2 mm increments. In some embodiments, bone growth promoting material may have a diameter of approximately 2 mm.

FIG. 2 illustrates an embodiment where an electrical bone growth stimulator 14 is implemented as a cathode mesh. As shown in FIG. 2, in this implementation, the electrical bone growth stimulator 14 may be comprised of a network of cathode material 28 that may be placed around at least a portion of bone growth promoting material 16. For instance, an implant 12 may include bone growth promoting material 16 surrounded, at least in part, by cathode material 28.

As illustrated in both FIG. 1 and FIG. 2, an electrical bone growth stimulator 14 may be connected to and/or in communication with a control unit 18. A control unit 18 may include or be in communication with an anode 20. In various embodiments, the control unit 18 and anode 20 may be part of the implant 12. However, the anode 20 may be located remotely from the fusion area. In this embodiment, the electrical bone growth stimulator 14 may plug into or otherwise be physically connected to the control unit 18.

In some embodiments, the surgical system includes an implant including integration of electronic components into the implant to monitor patient's recovery and may include an accelerometer.

In some embodiments, the cross-section geometry of implant 12 may have various configurations, such as, for example, cylindrical, round, oval, oblong, triangular, polygonal having planar or arcuate side portions, irregular, uniform, non-uniform, consistent, variable, horseshoe shape, U-shape or kidney bean shape.

An electrical bone growth stimulator 14 includes an electrically conductive material, such as, for example, a coating. In some embodiments, coating 50 is fabricated from titanium. Direct electric current is supplied to coating 50, as described herein, and coating 50 is configured to conduct electric current through tissue, bone graft tissue 16, interstitial tissue and/or fluids disposed adjacent to the implant. The electrical bone growth stimulator 14 conducts electric current in a configuration to generate a selected electric field in, around, about, through and/or adjacent to implant 12 to selectively stimulate bone growth in, around, about, through and/or adjacent implant 12.

The control unit 18 may include electronic components, such as, for example, a circuit board assembly, which includes one or more components for delivering electric current to the electrical bone growth stimulator 14, powering implant 12 and/or detecting/sensing diagnostics, and is suitable for implantation. In some embodiments, circuit board assembly is, for example, a flexible printed circuit.

The control unit 18 may be connected with and/or includes circuitry and one or more integrated circuits or micro-electronic chips for powering implant 12 and/or detecting/sensing diagnostics. In some embodiments, the one or more integrated circuits disposed within the control unit 18 can remotely communicate with electronic components of spinal implant system 10 disposed outside or external to a body of a patient. For instance, a control unit 18 may include one or more transmitters and/or receivers for facilitating wireless communication with electronic components disposed outside or external to a body of a patient. In some embodiments, the control unit 18 can remotely communicate with such external electronic components to power implant 12 and/or transfer, transmit and/or receive data relating to implant 12 including treatment and/or diagnostics, as described herein. In some embodiments, the remote communication can include a wireless link, such as, for example, Bluetooth, NFC, WiFi, MICS, and/or as described in U.S. Pat. No. 5,683,432 "Adaptive Performance-Optimizing Communication System for Communicating with an Implantable Medical Device" to Goedeke, et al., the contents of which being hereby incorporated by reference in its entirety.

In other embodiments, the control unit 18 can remotely communicate with electronic components of spinal implant system 10 disposed inside a body of a patient. For instance, the control unit 18 may power implant 12 and/or transfer, transmit and/or receive data relating to implant 12 including treatment and/or diagnostics.

Figure 3:
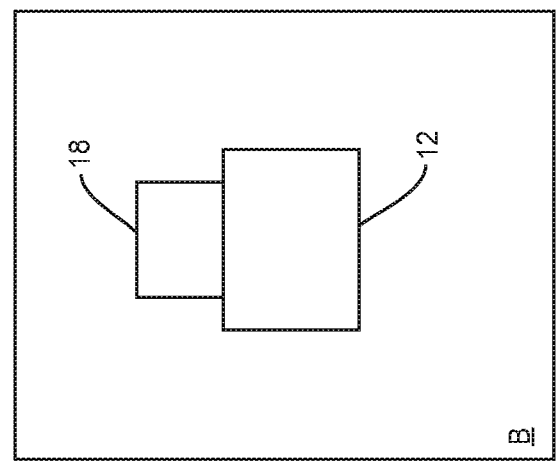
FIG. 3 illustrates example components of a surgical system according to an embodiment.
Figure 3:
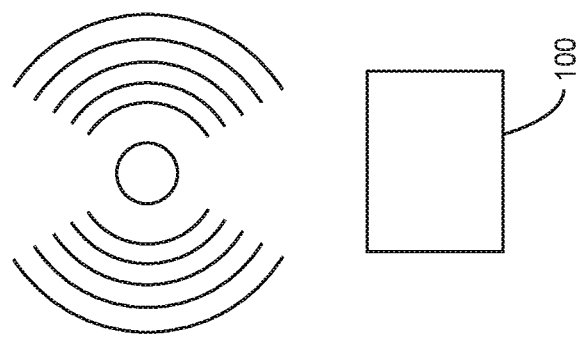
Figure 3:
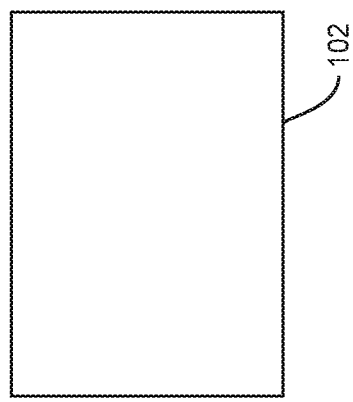

In some embodiments, the control unit 18 may communicate with a remote controller 100 located external to a patient's body as illustrated in FIG. 3. For instance, a remote controller 100 may be incorporated into or attached to a brace or other wearable item that a patient may wear such as, for example, a t-shirt, a harness, a jacket, a gown and/or the like. In this embodiment, the control unit 18 of the implant 12 may communication with the remote controller 100 via wireless, short range, or other communication protocols.

In some embodiments, the remote controller 100 may serve as a remote power source disposed outside or external to a body B of a patient. The control unit 18 of an implant 12 may be configured for inductive communication with remote controller 100 for power harvesting of a communication signal for powering implant 12. In some embodiments, remote controller 100 may include or be a component of a computer, a tablet, a smartphone, a cell phone, PDA, laptop, surgical instrument, clothing, accessory such as a belt, bag, wallet, pocketbook, backpack or other device.

The remote controller 100 may emit a small electric current to create a magnetic field that bridges the physical space between the remote controller and implant 12 implanted within body B. The remote controller 100 radiates energy through a cutaneous barrier, such as, for example, the skin of body B to adjacent implant 12. An electromagnetic field is generated by a transmitting coil within remote controller 100 to transmit power across the skin to the control unit 18 of the implant 12. The control unit 18 transfers the received power to implant 12 for charging/powering.

In some embodiments, as shown in FIG. 3, control unit 18 remotely communicates with a device, such as, for example, a computer 102 that is disposed outside or external to body B to transfer, transmit and/or receive data relating to implant 12 including treatment and/or diagnostic information obtained from implant 12. The control unit 18 may include diagnostic sensor electronics 92 connected with one or more sensors disposed about an electrical bone growth stimulator 14 to obtain and store data received from implant 12 and surrounding tissue. Diagnostic sensor electronics 92 may comprise various commercially available integrated circuit devices, see, for example, but not limited to, the AD5933 Impedance Converter Network Analyzer distributed by Analog Devices. Integrated circuit device may comprise various commercially available integrated circuit devices, see, for example, but not limited to, the RF430 microcontroller distributed by Texas Instruments RF430.

In some embodiments, diagnostic sensor electronics 92 gather information, such as, for example, loading information, pressure information, tension information, motion information, alignment or misalignment information and/or temperature, relating to implant 12 and/or treatment, as described herein. Computer 102 remotely communicates with control unit 18, as described herein, to collect data from implant 12 via diagnostic sensor electronics 92. In some embodiments, a reader 104 is disposed on body B that communicates with computer 102. In some embodiments, control unit 18, as described herein, includes reader 104. Reader 104 emits a small electric current that creates a magnetic field to bridge the physical space between reader 104 and implant 12. The electric field is received by the control unit 18 and converted into electrical impulses to communicate data and diagnostics, relating to implant 12 and/or treatment to computer 102, as described herein.

Diagnostic sensor electronics 92 provides feedback and/or measures one or more diagnostic conditions. In some embodiments, the diagnostics include, for example, embedded sensors for strain, stress and/or temperature. Diagnostic sensor electronics 92 sense and transmit to computer 102 various diagnostic indicia, and in some embodiments, diagnose and respond to such measurements, such as, for example, in the context of a spinal implant surgery. In some embodiments, a surgeon can monitor a patient after surgery, and make adjustments to implant 12 and/or treatment to avoid a subsequent surgery. In some embodiments, this configuration allows implant 12 and/or treatment to be corrected or modified based on changes that take place subsequent to surgery, and/or for selected and remote changes to diagnostic conditions inside body B. In some embodiments, diagnostic sensor electronics 92 may indicate fusion rate of implant 12 with vertebrae.

In some embodiments, diagnostic sensor electronics 92 sense or detect impedance and/or collect impedance measurements as a proxy/indicator of fusion based on configuration of tissue. In some embodiments, diagnostic sensor electronics 92 monitor diagnostic measurements of impedance or interpreting such impedance measurements as an indication of bone growth/fusion in, around, about, through and/or adjacent to implant 12. For example, in some embodiments, diagnostic sensor electronics 92 sense or detect impedance and/or collect impedance measurements based on the configuration of tissue such as fat, muscle, bone and blood.

In some embodiments, diagnostic sensor electronics 92 sense or detect impedance of fat tissue in a range of 2500 through 5000 ohms. In some embodiments, diagnostic sensor electronics 92 sense or detect impedance of transverse muscle in a range of 700 through 2500 ohms. In some embodiments, diagnostic sensor electronics 92 sense or detect impedance of long muscle in a range of 125 through 350 ohms. In some embodiments, diagnostic sensor electronics 92 sense or detect impedance of bone in a range of 1500 through 10000 ohms. In some embodiments, diagnostic sensor electronics 92 sense or detect impedance of blood in a range of 140 through 240 ohms. In one example, implant 12 selectively stimulates bone growth and diagnostic sensor electronics 92 sense a detectable diagnostic of tissue adjacent implant 12 that detects an impedance measurement of 200 ohms corresponding to blood and an impedance measurement of 5000 ohms corresponding to bone.

In some embodiments, the components of implant 12 can be selected for a particular surgical procedure and/or from alternate components of a spinal implant kit based on one or more criteria. In some embodiments, the one or more criteria include, for example, anatomical parameters, implant parameters and/or surgical procedure parameters, as described herein. In some embodiments, the anatomical parameters can include condition, quality, configuration and/or dimension of selected anatomy, for example, one or more disc space dimensions, disc height, disc tissue, and/or one or more vertebra dimensions, vertebra/vertebrae height and/or vertebral tissue, and/or a footprint associated with vertebral tissue including vertebrae and intervertebral discs. In some embodiments, the footprint can include the area defined by vertebral tissue, such as, for example, an endplate surface of one or more vertebra.

In some embodiments, the implant parameters can include predetermined and/or preselected implant size, predetermined and/or preselected implant height, predetermined and/or preselected footprint, targeted implant size, targeted implant height, targeted footprint and/or materials. In some embodiments, the surgical procedure parameters can include one or a plurality of vertebra, uni-lateral treatment, bi-lateral treatment, PLIF, TLIF, DLIF, ACDF, OLIF and/or ALIF. In some embodiments, the components of implant 12 can be selected prior to surgery. For example, a surgeon can conduct imaging diagnosis and/or pre-operative planning using medical imaging, as described herein, to measure anatomical parameters employed to determine implant parameters. In some embodiments, one or more members can be selected for assembly of a personalized implant 12 with predetermined footprint size and target height based on implant footprint size.

Figure 4A:
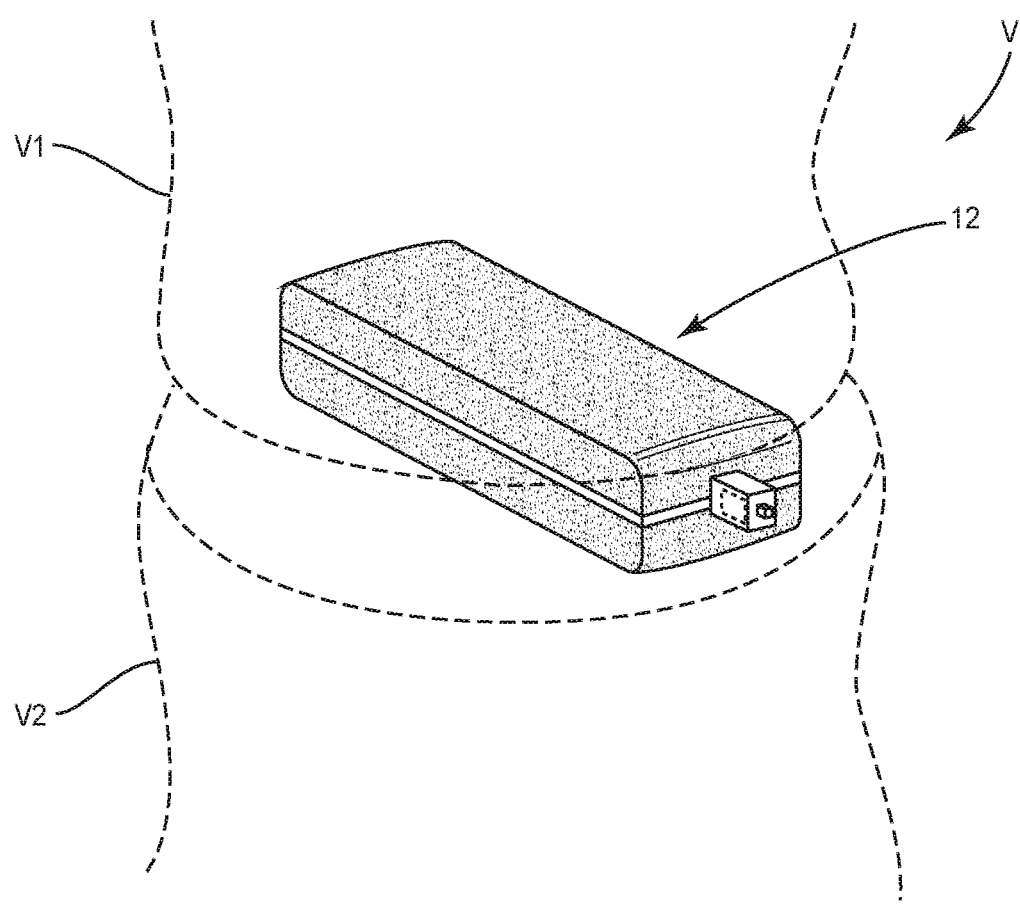
FIGS. 4A and 4B illustrate an example spinal surgery system according to various embodiments.
Figure 4B:
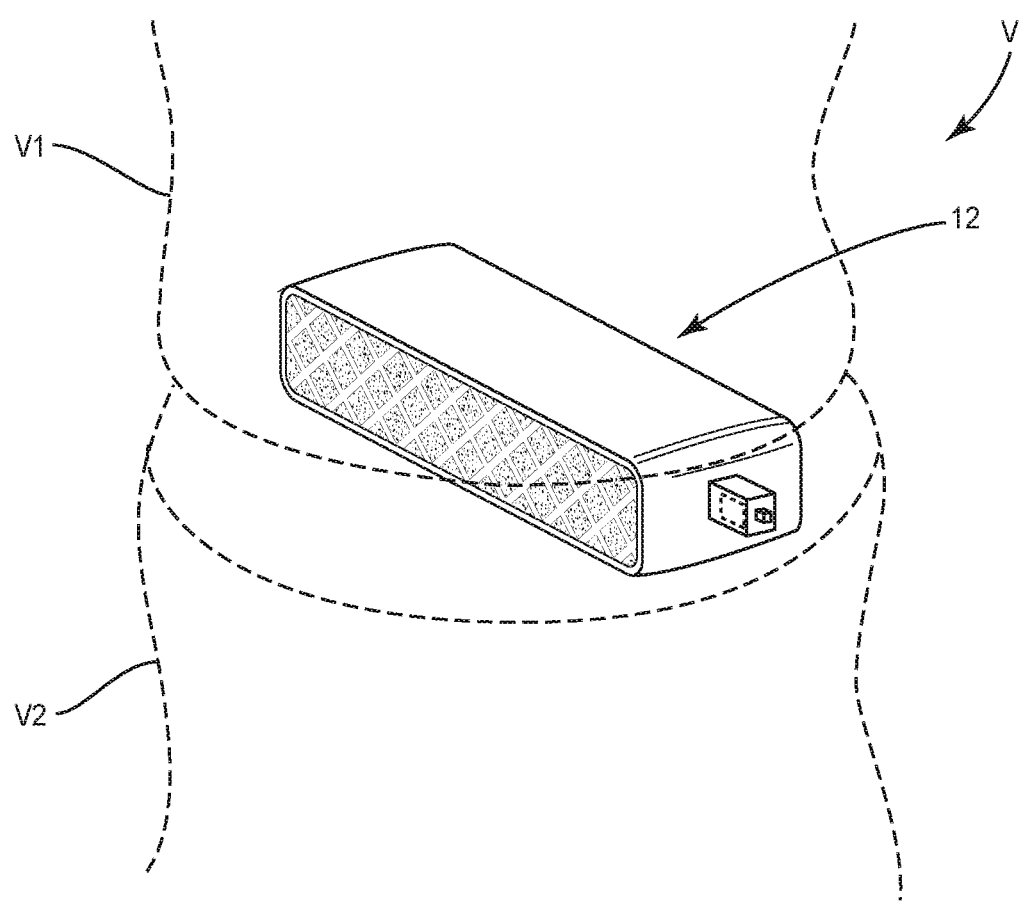

In assembly, operation and use, as shown in FIG. 4A and FIG. 4B, spinal implant system 10, similar to the systems and methods described herein, is disposed with tissue, such as, for example, vertebrae V of a patient body B for treatment of a spinal disorder, such as those described herein, affecting a section of a spine of a patient. Spinal implant system 10 may also be employed with other surgical procedures.

Electrical stimulation across the anode 20 and the electrical bone growth stimulator 14 facilitates fusion of implant 12 with bone tissue of vertebrae V1, V2. The anode 20 and electrical bone growth stimulator 14 generate electric field EF adjacent implant 12 to selectively stimulate tissue growth adjacent the electrical bone growth stimulator 14, as described herein.

Figure 5A:
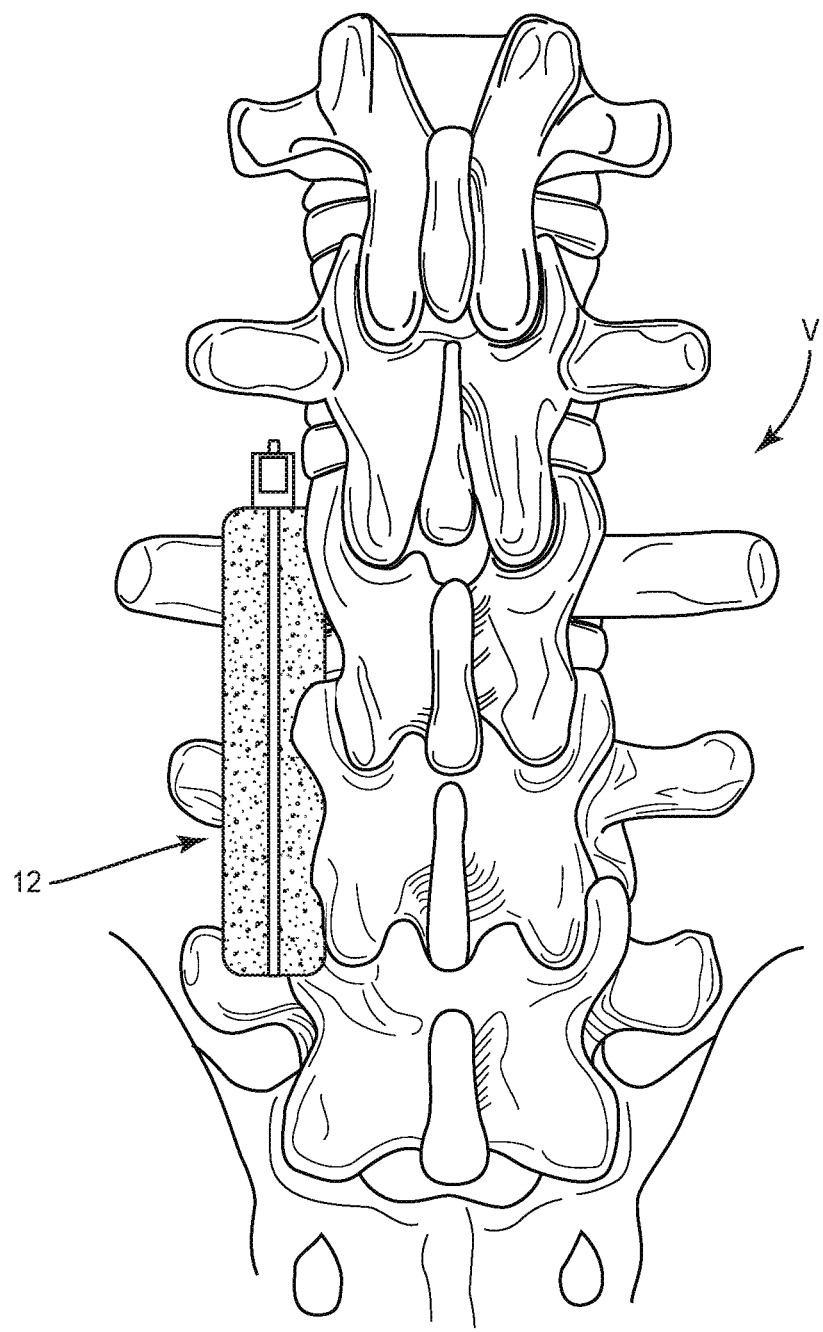
FIGS. 5A and 5B illustrate an example spinal surgery system according to various embodiments.
Figure 5B:
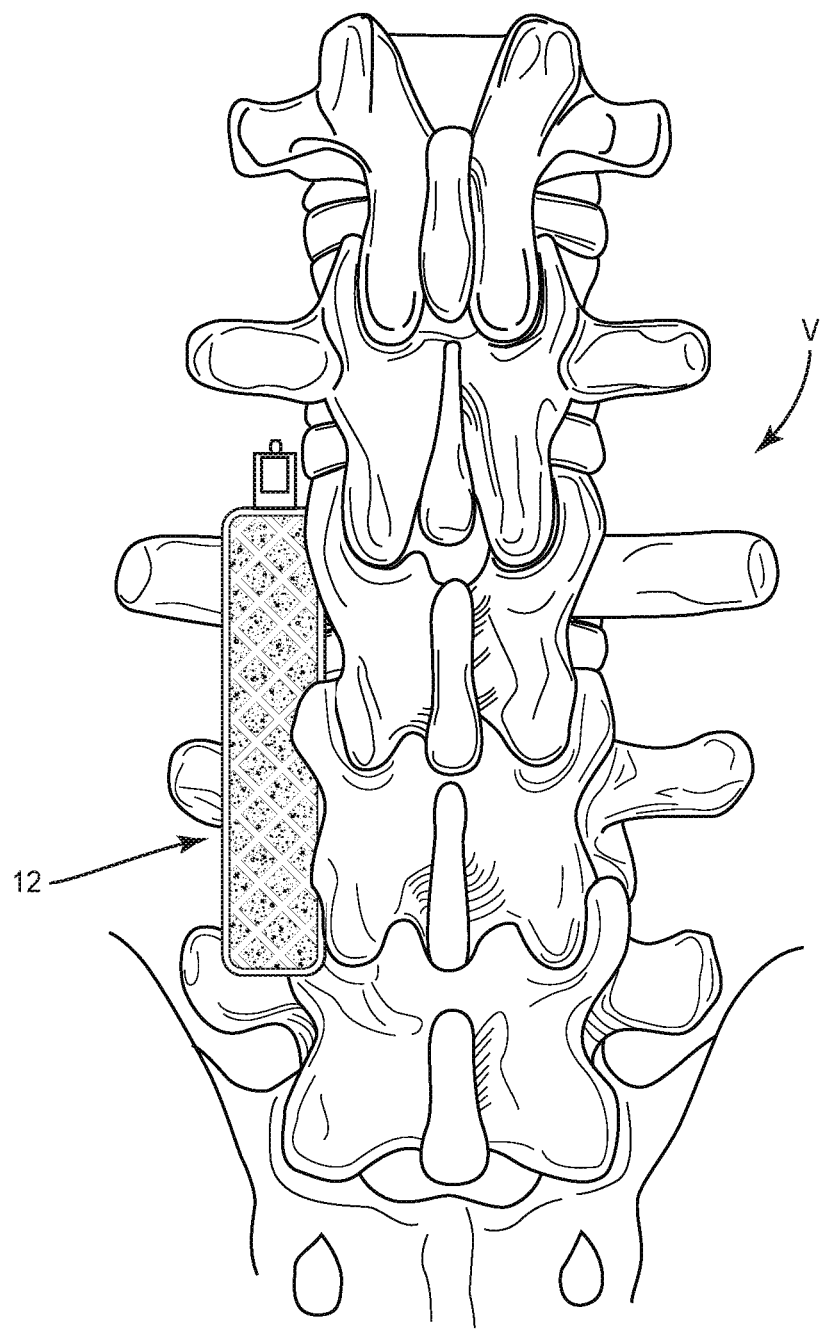

In various embodiments, as shown in FIG. 5A and FIG. 5B, spinal implant system 10, similar to the systems and methods described herein, may be used in posterior spinal fusion. At least a portion of the spinal implant system 10 may be placed along or within a patient's lateral gutters, as illustrated in FIGS. 5A and 5B. Electrical stimulation across the anode 20 and the electrical bone growth stimulator 14 facilitates fusion of implant 12 with one or more gutters. The anode 20 and electrical bone growth stimulator 14 generate electric field EF adjacent implant 12 to selectively stimulate tissue growth adjacent the electrical bone growth stimulator 14, as described herein.

Diagnostic sensor electronics 92 provide feedback and/or measure diagnostic conditions of the vertebrae. Diagnostic sensor electronics 92 sense and transmit to computer 102 various diagnostic indicia, and also diagnoses and responds to such measurements, such as, for example, in the context of a spinal implant surgery, a surgeon can monitor a patient after or during surgery, and make adjustments to implant 12 or treatment, as described herein.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiopaque markers may be included for identification under x-ray, fluoroscopy, CT, MRI or other imaging techniques. In some embodiments, the use of surgical navigation, microsurgical and image guided technologies may be employed to access, view and repair spinal deterioration or damage, with the aid of spinal implant system 10. In some embodiments, spinal implant system 10 may include one or a plurality of plates, connectors and/or bone fasteners for use with a single vertebral level or a plurality of vertebral levels.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant system comprising:
    bone growth promoting material;
    an electrical bone growth stimulator comprising a first end, a second end and a body portion disposed between the first end and the second end, wherein the electrical bone growth stimulator is positioned across a portion of the bone growth material, wherein the electrical bone growth stimulator is configured to conduct an electric current to stimulate tissue growth adjacent to the electrical bone growth stimulator; and
    an anode located remotely from the electrical bone growth stimulator.

2. The spinal implant system of claim 1, wherein the bone growth promoting material comprises one or more of the following:
    synthetic bone grafting material;
    allograft bone grafting material; or
    bone morphogenetic protein material.

3. The spinal implant system of claim 1, wherein the electrical bone growth stimulator comprises a cathode rod.

4. The spinal implant system of claim 1, further comprising a control unit having one or more of the following:
    a transmitter; or
    a receiver.

5. The spinal implant system of claim 4, wherein the control unit is configured to communicate with a remote controller.

6. The spinal implant system of claim 5, wherein the electrical bone growth stimulator is configured to be powered by the remote controller.

7. The spinal implant system of claim 1, further comprising a control unit, wherein the control unit comprises one or more diagnostic sensors that are configured to detect impedance between the electrical bone growth stimulator and the anode.

8. A spinal implant system comprising:
    bone growth promoting material; and
    an electrical bone growth stimulator comprising a mesh that surrounds at least a portion of the bone growth material, wherein the electrical bone growth stimulator is configured to conduct an electric current to stimulate tissue growth adjacent to the electrical bone growth stimulator.

9. The spinal implant system of claim 8, wherein the bone growth promoting material comprises one or more of the following:
    synthetic bone grafting material;
    allograft bone grafting material; or
    bone morphogenetic protein material.

10. The spinal implant system of claim 8, further comprising a control unit and an anode, wherein the control unit comprises one or more of the following:
    a transmitter; or
    a receiver.

11. The spinal implant system of claim 10, wherein the control unit is configured to communicate with a remote controller.

12. The spinal implant system of claim 11, wherein the electrical bone growth stimulator is configured to be powered by the remote controller.

13. The spinal implant system of claim 8, further comprising a control unit, wherein the control unit comprises one or more diagnostic sensors that are configured to detect impedance between the electrical bone growth stimulator and a remote anode.

14. A bone graft comprising:
    bone growth promoting material; and
    an electrical bone growth stimulator comprising cathode material, wherein the electrical bone growth stimulator is positioned across at least a portion of the bone growth material, wherein the electrical bone growth stimulator is configured to:
    conduct an electric current to stimulate tissue growth adjacent to the electrical bone growth stimulator; and
    communicate with an anode located remotely from the bone graft.

15. The bone graft of claim 14, wherein the bone growth promoting material comprises one or more of the following:
    synthetic bone grafting material;
    allograft bone grafting material; or
    bone morphogenetic protein material.

16. The bone graft of claim 14, wherein the electrical bone growth stimulator comprises a cathode rod.

17. The bone graft of claim 14, wherein the electrical bone growth stimulator comprises a cathode mesh.

18. The bone graft of claim 14, further comprising a control unit having one or more of the following:
    a transmitter; or
    a receiver.

19. The bone graft of claim 18, wherein the control unit is configured to communicate with a remote controller.

20. The bone graft of claim 14, further comprising a control unit, wherein the control unit comprises one or more diagnostic sensors that are configured to detect impedance between the electrical bone growth stimulator and the remote anode.

* * * * *